(12) United States Patent
Nasser-Ghodsi et al.

(10) Patent No.: US 6,801,596 B2
(45) Date of Patent: Oct. 5, 2004

(54) METHODS AND APPARATUS FOR VOID CHARACTERIZATION

(75) Inventors: Mehran Nasser-Ghodsi, Hamilton, MA (US); Anne Testoni, Marlborough, MA (US); Steve Oestreich, Mesa, AZ (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 330 days.

(21) Appl. No.: 09/990,171

(22) Filed: Nov. 21, 2001

(65) Prior Publication Data

US 2003/0063705 A1 Apr. 3, 2003

Related U.S. Application Data

(60) Provisional application No. 60/326,621, filed on Oct. 1, 2001.

(51) Int. Cl.⁷ .............................................. G01N 23/06
(52) U.S. Cl. .............................. 378/53; 378/54; 378/57
(58) Field of Search ............................. 378/53, 54, 57, 378/58, 98.8, 83, 55, 146, 206; 250/310, 307, 306; 356/237.1

(56) References Cited

U.S. PATENT DOCUMENTS

| | | |
|---|---|---|
| 4,162,528 A | 7/1979 | Maldonado et al. |
| 4,472,825 A | 9/1984 | Jenkins |
| 4,476,386 A | 10/1984 | Reid et al. |
| 4,534,049 A | 8/1985 | Koga |
| 4,675,889 A | 6/1987 | Wood et al. |
| 4,777,364 A | 10/1988 | Sartore |
| 4,885,465 A | 12/1989 | Nagatsuka et al. |
| 4,959,848 A | 9/1990 | Parobek |
| 4,962,516 A | 10/1990 | Soezima |
| 5,055,679 A | 10/1991 | Ninomiya et al. |
| 5,060,247 A | 10/1991 | Watanabe |
| 5,065,020 A | 11/1991 | Kanda |
| 5,210,414 A | 5/1993 | Wallace et al. |
| 5,299,252 A | 3/1994 | Takahashi |
| 5,350,921 A | 9/1994 | Aoyama et al. |
| 5,485,499 A | 1/1996 | Pew et al. |
| 5,530,732 A | 6/1996 | Takemi |
| 5,594,246 A | 1/1997 | Sudo et al. |
| 5,596,195 A | 1/1997 | Obori et al. |
| 5,656,812 A | 8/1997 | Takahashi |
| 5,657,363 A | 8/1997 | Hossain et al. |
| 5,703,361 A | 12/1997 | Sartore |
| 5,705,878 A * | 1/1998 | Lewis et al. ................. 310/328 |
| 5,754,620 A | 5/1998 | Hossain et al. |
| 5,777,336 A | 7/1998 | Silver et al. |
| 5,866,903 A | 2/1999 | Morita et al. |
| 5,877,498 A | 3/1999 | Sugimoto et al. |
| 5,892,809 A | 4/1999 | Wittry |
| 5,926,522 A | 7/1999 | McCarthy et al. |
| 6,108,398 A | 8/2000 | Mazor et al. |
| 6,351,516 B1 | 2/2002 | Mazor et al. |
| 6,353,222 B1 | 3/2002 | Dotan ......................... 250/310 |
| 6,421,122 B2 | 7/2002 | Nara et al. |
| 6,469,312 B2 * | 10/2002 | Agano ........................ 250/580 |

OTHER PUBLICATIONS

J.L. Pouchou and F. Pichoir, "Electron Probe X–Ray Microanalysis Applied To Thin Surface Films and Stratified Specimens", Scanning Microscopy, Supplement 7., (1993), pp. 167–189.

(List continued on next page.)

*Primary Examiner*—Craig E. Church
*Assistant Examiner*—Irakli Kikndze
(74) *Attorney, Agent, or Firm*—Beyer Weaver & Thomas, LLP

(57) ABSTRACT

The present invention provides a system for characterizing voids in test samples. An x-ray emission inducer scans a target such as a via on a test sample. A metallization or thin film layer emits x-rays as a result of the scan. The x-ray emission intensity can be measured and compared against a control measurement. The information obtained can be used to characterize a void in the scan target.

41 Claims, 11 Drawing Sheets

OTHER PUBLICATIONS

"High–Resolution X–ray Microanalysis for Low Voltage Applications", Noran Instruments, (1997), 5 pages.

M. Stavrev[a], D. Fischer[a], C. Wenzel[a], and T. Heiser[b], "Study of Ta(N,O) diffusion barrier stability: analytical and electrical characterization of low level Cu contamination in Si", Microelectronic Engineering, 37/38 (1997) pp. 245–251.

JeanLouis Pouchou, "X–Ray microanalysis of stratified specimens", Elsevier Science Publishers B.V., Analytica Chimica Acta. 283 (1993) pp. 81–97.

Schiebl et al., "A characteristic fluorescence correction factor for use in electron probe microanalysis", Microsc. Microanal, Microstruct. 2, 1991, pp. 413–423.

S. Sevov et al., "A comparison of recently developed correction procedures for electron probe microanalysis", Scanning, 1989, vol. 11, pp. 123–134.

August et al., "A method for determining the mass thickness of thin films using electron probe microanalysis", Scanning, 1987, vol. 9, pp. 145–155.

August et al., "Energy distribution of electrons transmitted through thin foils", Institut fur Angewandte aund Technische Physik, Technische Universitat Wien Wiedner Hauptstr.8–10, A–1040 Wien (Vienna), Austria.

Pfeiffer et al., "Models and their implementation", CEC–Vienna Reports, No. 92–08, Dec., 1992.

"MuFilm Data Collection & K–Ratio Measurement Documentation", pp. 2–10.

August et al., "Calculation and Comparison of the Surface Ionization", Institut fur Angewandte und Technische Physik, Technische Universitat Wien, Wiedner Hauptstr. 8–10, A–1040 Wien (Vienna), Austria.

August et al., "Calculation and Comparison of the Backscattering Factor R for Characteristic X–Ray Emission", Scanning, 1988, vol. 10, pp. 107–113.

August et al., "The Backscattering Factor as a Part of the Correction Procedures Employed in Quantitative Electron Probe Microanalysis", Radex–Rundschau, 1988, pp. 624–637.

August et al., "Calculation of the electron backscattering coefficient for thin films using a simple electron scattering model", J. Microsc. Spectrose. Electron., 1989, vol. 14, pp. 189–201.

August, et al., "Theoretical prediction of the electron backscattering coefficient for multilayer structures", Journal of Microscopy, Feb. 1990, vol. 157, pp. 247–254.

\* cited by examiner

Die2 No void, x-ray measurement

METHODS AND APPARATUS FOR VOID CHARACTERIZATION

CROSS-REFERENCE TO RELATED APPLICATIONS

This application claims the benefit of provisional application No. 60/326,621 filed Oct. 1, 2001.

The present application is related to concurrently filed U.S. patent application Ser. No. 09/990,170 by Mehran Nasser-Ghodsi and Jeffrey Reichert, and titled Methods and Apparatus for Void and Erosion Localization. The present application is also related to U.S. patent application Ser. No. 09/695,726 by Shing Lee, and titled Film Thickness Measurement Using E-Beam Induced X-Ray Microanalysis as of filing on Oct. 23, 2000. Each of the above noted applications are incorporated herein by reference for all purposes.

BACKGROUND OF THE INVENTION

1. Field of the Invention

The present invention generally relates to the field of inspection and analysis of specimens and, more particularly, to void characterization in integrated circuits.

2. Description of Related Art

The metallization and thin film layers of conventional integrated circuits contain interconnects such as vias, contacts, and windows. The interconnects are arranged to allow electrical contact between transistors and other circuitry in the integrated circuit. However, a variety of factors may cause the formation of voids in the conductive layers. Voids can interfere with electrical contact between various circuit elements. Voids may be caused by factors such as stress, electromigration, and impurities. As line widths continue to decrease in size, even relatively small voids are extremely harmful. Voids can lead to open circuits and ultimately failure of the integrated circuit.

Inspection of integrated circuit at various stages of manufacture can significantly improve production yield and product reliability. If a void can be detected early in production, the cause of the void can be determined and corrected before a significant number of defective IC's are manufactured.

Conventional defect detection systems frequently use the "voltage contrast" technique. The voltage contrast technique operates on the basis that potential differences in the various locations of a sample under examination cause differences in secondary electron emission intensities when the sample is the target of an electron beam. Thus, the potential state of the scanned area is acquired as a voltage contrast image such that a low potential portion of, for example, a wiring pattern might be displayed as bright (intensity of the secondary electron emission is high) and a high potential portion might be displayed as dark (lower intensity secondary electron emission). Alternatively, the system may be configured such that a low potential portion might be displayed as dark and a high potential portion might be displayed as bright.

A secondary electron detector is used to measure the intensity of the secondary electron emission that originates only at the path swept by the scanning electron beam. A defective portion can be identified from the potential state of the portion under inspection. In one form of inspection, the mismatched portion between the defective voltage contrast image and the defect free one reveals the general defect location.

Other techniques for defect detection involve slicing a wafer into cross sections and using an electron microscope to locate defects. Intrusive methods, however, are both time consuming and wasteful. Acoustic and optical methods are also available, but can only be used in very particular circumstances. The acoustic techniques require significantly more time to collect adequate data for a statistically significant sample. Additionally the acoustic techniques can not address transparent films and are limited in the lower (few nanometer) film thickness range.

Using the voltage contrast technique allows a general determination of the location of defects in the sample. However, conventional voltage contrast techniques do not allow thorough characterization of a void. For example, voltage contrast does not provide sufficient information about the type of defect, size, or exact location including the depth of the void. Accordingly, improved detection systems allowing more precise characterization of voids are desirable.

SUMMARY

The present invention provides a system for characterizing voids in test samples. An x-ray emission inducer scans a target such as a via on the test sample. A metallization or thin film layer emits x-rays as a result of the scan. The x-ray emission intensity can be measured and compared against a control measurement. The information obtained can be used to characterize a void in the scan target.

In one embodiment, an apparatus for characterizing a void in a first scan target associated with a sample having a first surface and a second surface is provided. An x-ray emission inducer is configured to scan a first scan target. The x-ray emission inducer causes the first scan target to emit x-rays from the first surface. An x-ray emission detection system is configured to obtain a measurement of the x-rays emitted from the first surface of the sample. The x-ray measurement is compared to a control measurement to characterize a void in the first scan target.

In another embodiment, a system for characterizing voids associated with a sample having a first surface and a second surface is provided. The system includes a memory and a processor coupled with memory. The processor is configured to identify a first measurement of induced x-ray emissions characteristic of a first material at a first scan target, identify a control measurement, and provide the first measurement and the control measurement for comparison to thereby obtain information for characterizing a void associated with the first scan target in the sample.

In still another embodiment, a method for characterizing a void in a sample is provided. A first measurement of induced x-ray emissions characteristic of a first material at a first scan target is identified. A control measurement is identified. The first measurement and the control measurement are provided for comparison to thereby obtain information for characterizing a void associated with the first scan target in the sample.

These and other features and advantages of the present invention will be presented in more detail in the following specification of the invention and the accompanying figures which illustrate by way of example various principles of the invention.

BRIEF DESCRIPTION OF THE DRAWINGS

The invention may best be understood by reference to the following description taken in conjunction with the accompanying drawings. It should be noted that the drawings are illustrative of specific embodiments of the present invention.

DESCRIPTION OF SPECIFIC EMBODIMENTS

Figure 1:
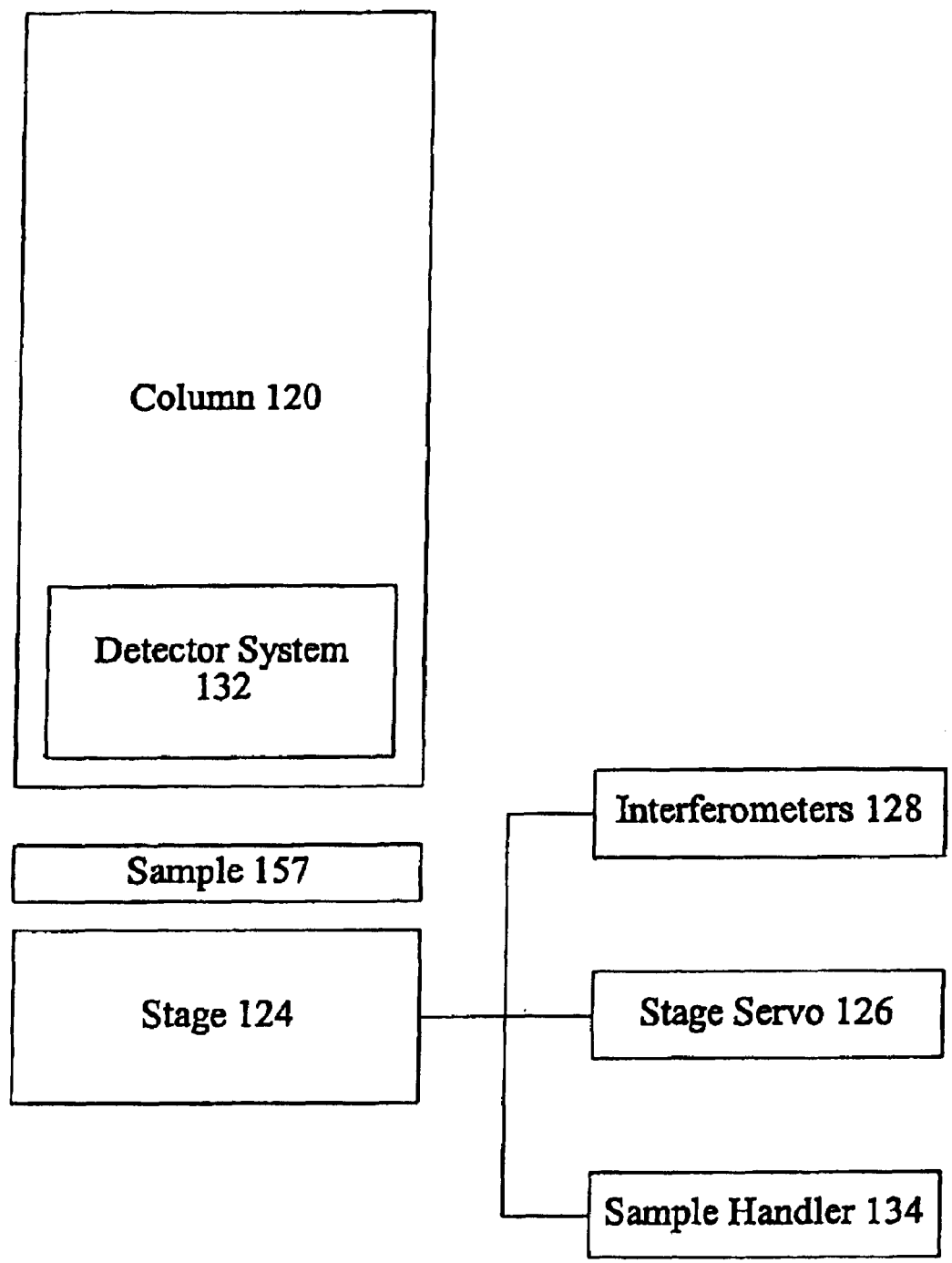
FIG. 1 is a diagrammatic representation of a system that can use the techniques of the present invention.

As will be further described below, specific embodiments of the present invention provide efficient wafer inspection capabilities in order to detect, isolate and characterize voids in test samples.

Several embodiments of the present invention are described herein in the context of exemplary multilevel integrated circuit structures, including semiconductor structures and overlying metallization or other interconnects, using various levels of conductors that are separated from each other and the substrate by dielectric layers. However, structures formed using other methods of semiconductor fabrication also fall within the scope of the present invention.

The techniques of the present invention allow nondestructive detection, isolation, and characterization of voids in a test sample. In one embodiment, the test sample is a wafer comprising a plurality of integrated circuits. During the production of conventional integrated circuits, openings are typically left in a dielectric layer for a conductive material having low resistivity. The openings may be filled with the conductive material, such as aluminum or copper, to allow electrical contact between circuit elements. The openings can be referred to as vias, windows, or contacts.

When the openings are filled with the conductive material, the integrated circuit elements can operate properly. However, a variety of factors may cause the formation of voids in the conductive material. The voids may be generated due to stress, electromigration, or impurities. As line widths continue to decrease in size, even relatively small voids can become detrimental. The voids can ultimately lead to failure of the integrated circuit by causing open circuits.

The present invention provides methods and apparatus for not only detecting and locating voids in a test sample, but also provides techniques for characterizing voids. The techniques allow a determination of void size and depth. With information about the characteristics of the voids, a system operator can improve the integrated circuit manufacturing process to reduce the number of voids and to increase yields.

In one embodiment, an x-ray emission inducer is used to scan a test sample. Any apparatus that is capable of causing a test sample to emit x-rays is referred to herein as an x-ray emission inducer. In one example, the x-ray emission inducer is an electron beam. In another example, the x-ray emission inducer is an irradiation source. The main sources used for generating x-rays are either electron beam or x-ray sources. One could generate x-rays using ion beams however, the ion beam will affect the substrate in the process either through implantation or through etching. The x-ray emission inducer scans a target site on the test sample. The target site may comprise a single via, window, or contact. An x-ray detector is aligned near the x-ray emission inducer to detect x-rays emitted from the test sample. According to various embodiments, a conductive material exposed to a scan emits x-rays with emission energies corresponding to the conductive material. For example, copper bombarded by electrons emits x-rays characteristic of copper while tantalum bombarded by electrons emits x-rays characteristic of tantalum. A scanned void having substantially no conductive material would not emit as many x-rays characteristic of the conductive material as a scanned piece of conductive material. An x-ray detector can measure the intensity of x-rays emitted at a scan target to determine characteristics of the void at the scan target. One benefit of using x-rays versus secondary electrons is that secondary electrons do not provide the information for a voided substrate, particularly for a deep void.

FIG. 1 is a diagrammatic representation of a system that can use the techniques of the present invention. The detail in FIG. 1 is provided for illustrative purposes. One skilled in the art would understand that variations to the system shown in FIG. 1 fall within the scope of the present invention. For example, FIG. 1 shows the operation of an x-ray emission inducer with a continuously moving stage. However, the test structures and many of the methods described herein are also useful in the context of other testing devices, including x-ray emission inducers operated in step and repeat mode. As an alternative to moving the stage with respect to the bean, the beam may be moved by deflecting the field of view with an electromagnetic lens. Alternatively, the beam column can be moved with respect to the stage.

Sample 157 can be secured automatically beneath an x-ray emission inducer 120. The x-ray emission inducer 120 can be a particle beam such as an electron beam or an irradiation source such as an x-ray emitter. The sample handler 134 can be configured to automatically orient the sample on stage 124. The stage 124 can be configured to have six degrees of freedom including movement and rotation along the x-axis, y-axis, and z-axis. In a specific embodiment, the stage 124 is aligned relative to the x-ray emission inducer 120 so that the x-directional motion of the stage is corresponds to the axis determined by the length of a via. For example, the sample 157 can be aligned so that the x-directional movement of the stage corresponds to the length of a via as viewed from the top of the sample. Similarly, the sample 157 can be aligned so that the x-directional movement of stage corresponds to the width of a via. Fine alignment of the sample can be achieved manually or automatically. The position and movement of stage 124 during the analysis of sample 157 can be controlled by stage servo 126 and interferometers 128.

While the stage 124 is moving in the x-direction, the inducer 120 can be repeatedly deflected back and forth in the y-direction. According to various embodiments, the inducer 120 is moving back and forth at approximately 100 kHz.

According to a specific embodiment, the axis formed by the x-ray emission detector 132 and the sample 157 is arranged at a 35-degree angle relative to the axis formed by x-ray emission inducer 120 and the sample 157. As will be appreciated by one of skill in the art, a close arrangement of inducer 120 and detector 132 allows accurate detection of x-ray emissions. The inducer 120 and detector 132 as well as other elements such as the stage can be controlled using a variety of processors, storage elements, and input and output devices.

Figure 2:
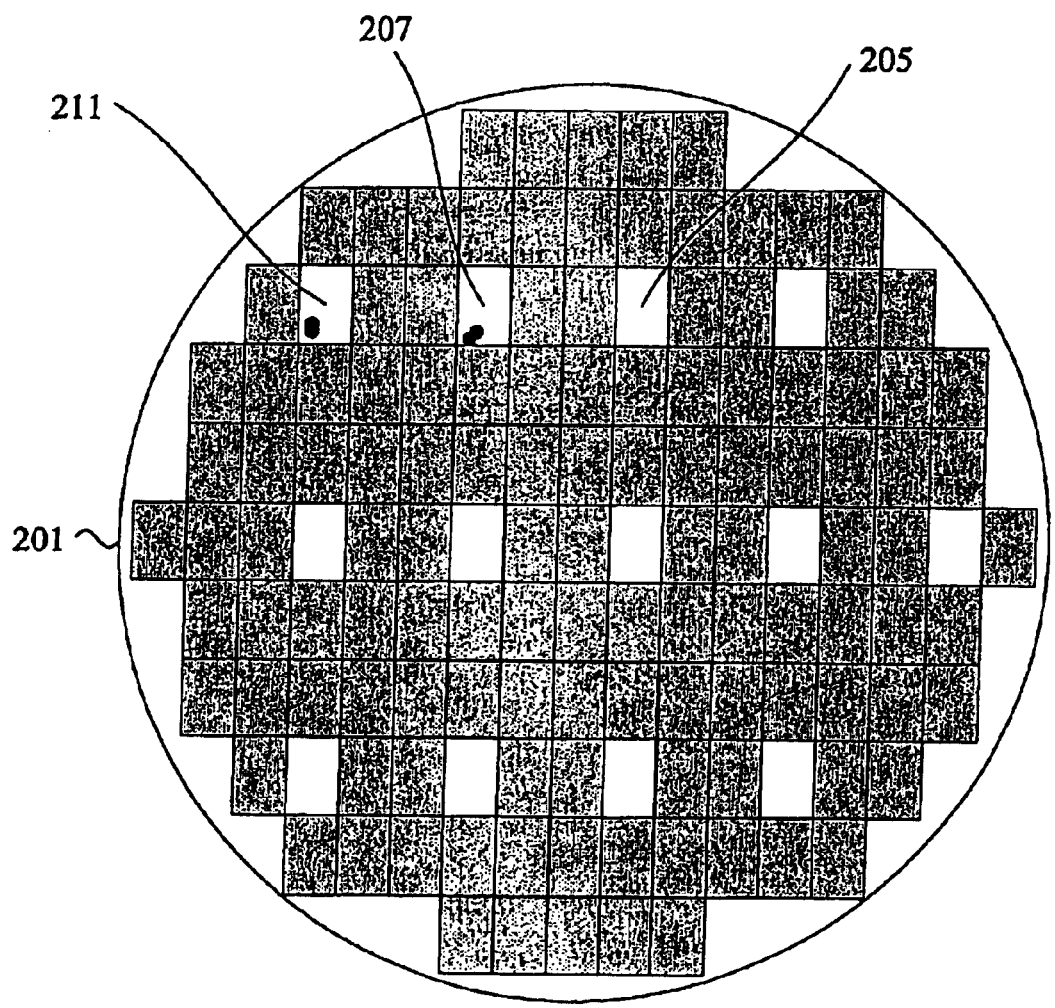
FIG. 2 is a diagrammatic representation of a wafer that may be the sample under test.

FIG. 2 is a diagrammatic representation of a wafer that may be a sample under test. A wafer 201 comprises a plurality of dies 205, 207, and 211. Die 205 contains no voids while dies 207 and 211 contain voids. According to various embodiments, the techniques of the present invention for void detection and characterization are performed after each metallization or thin film layer is deposited onto a wafer. The side of the wafer where the metallization process is performed is herein referred as the top surface of the wafer. The wafer can be scanned to detect and characterize voids after a thin film layer or metallization layer comprising a material such as copper is deposited onto the first surface of the wafer. The ability to detect voids during the manufacturing process allows immediate modification of the manufacturing process. By contrast, conventional techniques often were unable to recognize and correct defects and defective processes until after processing of the devices was complete.

The test methodologies of the present invention can be used as part of an advanced process control system, in which data from the testing process is provided to automated control systems for improving process yield. As an example, the techniques for void detection can provide data to automated control systems that dynamically improve the metallization processes.

Figure 3:
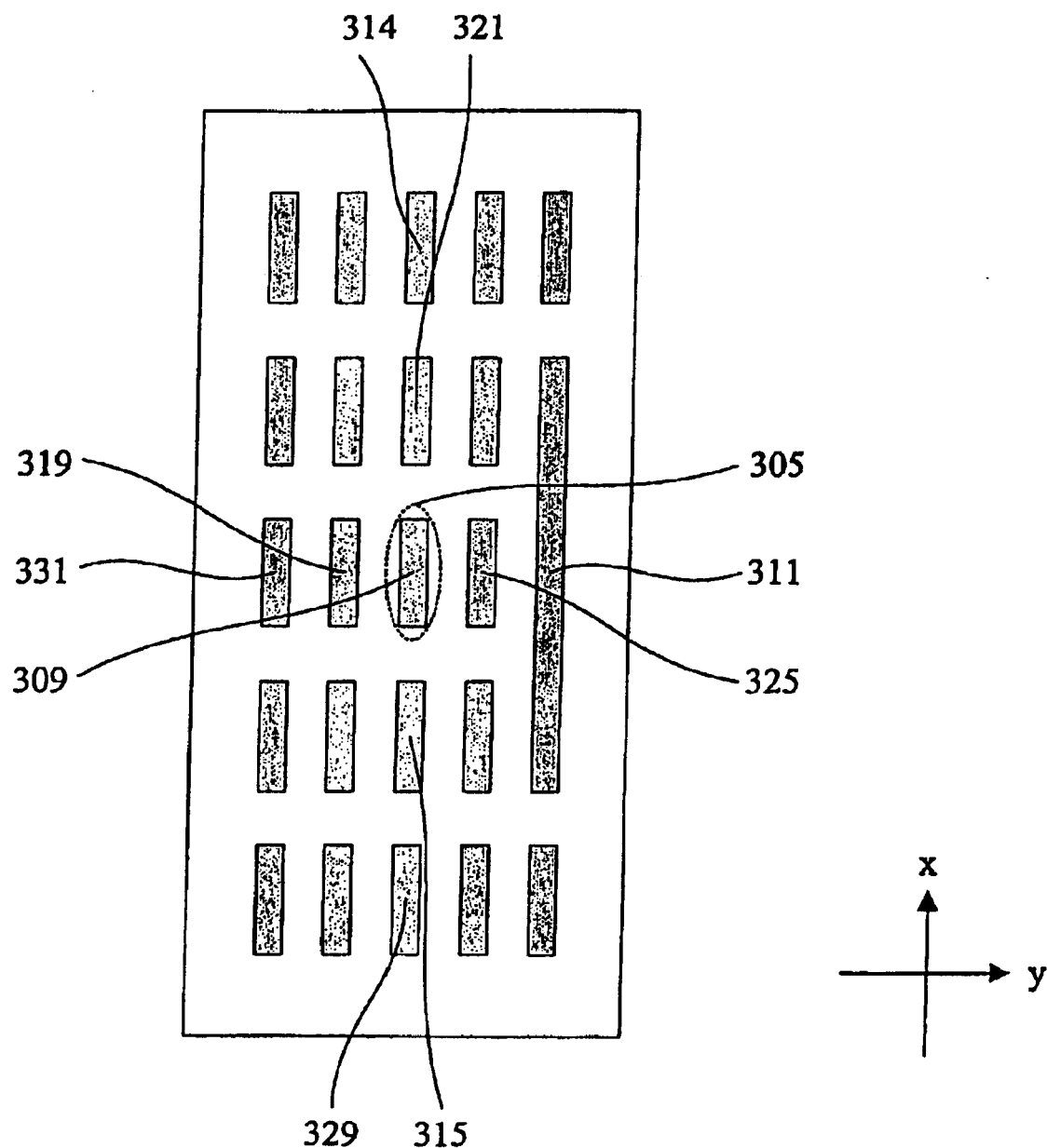
FIG. 3 is a diagrammatic representation of a plurality of vias on an integrated circuit.

FIG. 3 is a diagrammatic representation of a plurality of vias formed as part of a metallization layer on a die. As noted above, vias are one possible scan target for the x-ray emission inducer. Other scan targets include conductive elements such as contacts and windows. Contacts are generally larger than vias and are single layer structures. Vias generally connect layers vertically to each other.

As will be appreciated by one of skill in the art, vias can have a variety of different configurations. There may be 6 million vias formed in a single metallization layer of a die. According to various embodiments, each via is a scan target. In one example, the scan target is 1.29 μm. An x-ray emission inducer is targeted at each individual via and an x-ray emission detector is used to measure the amount of x-rays emitted due to the scan. Via 309 may reside in scan target 305. Sample 301 may be rotated into a position so that that the length axis of via 309 is substantially parallel to the x-directional movement of the stage. It should be noted that measuring x-ray emissions resulting from the scanning of a particular via may require realignment of the sample with respect to the x-ray emission inducer.

Vias 319, 321, 311, and 315 are adjacent to via 309. Via 321 is referred to herein as the via in the +x position of via 309. Via 315 is referred to herein as the via in the −x position of via 309. Similarly, vias 319 and 311 are referred to herein as the vias in the +y and −y positions of via 309.

According to one embodiment, via 309 in scan target 305 is bombarded by electrons from an electron beam. The electrons from the electron beam cause the conductive material of via 309 to emit x-rays. The x-ray detector can then measure the characteristic x-ray emissions to determine whether a void exists in via 309. However, when the electrons are directed at scan target 305, some of the electrons reach adjacent vias 321, 311, 315, and 319. The electrons reaching the adjacent vias cause the adjacent vias to emit x-rays as well. These x-rays may also be measured by the x-ray detector, skewing the x-ray emission measurement for via 309. Adjacent vias are referred to herein as adjacent scan targets. In one embodiment, the control measurement may be determined by scanning the adjacent vias or adjacent scan targets. Adjacent vias provide an effective technique for providing a control measurement because adjacent vias often have characteristics similar to that of the via under test.

According to one embodiment, the x-ray emission measurement resulting from the scan of scan target 305 is compared to a control measurement to allow consideration of skew. Alternatively, the control measurement may be obtained from the design database having values for vias of a particular material. In one embodiment, if the x-ray measurement for the via under test is greater than or equal to the control measurement, there is no void in the via. If the x-ray measurement for the via is less than the control measurement, there is a void in the via.

For example, a via 309 without a void in a copper metallization layer will have a comparable x-ray emission measurement as an adjacent via 311 without a void. However, a via 309 with a void will not have the same x-ray emission measurement as an adjacent via 311 without a void. More specifically, many x-ray emissions from a via 311 without a void will have energy levels corresponding to copper. The x-ray emissions from a via 309 with a void will have fewer emissions with energy levels corresponding to copper. Some emissions will still be detected, as the x-ray emissions may be emissions from copper surrounding the void or from neighboring vias.

According to one embodiment, the x-ray emissions resulting from scanning vias 341, 321, 311, 325, 315, 329, 331, and 319 are used to obtain a control measurement. If the average of the x-ray emissions resulting from scanning the above adjacent vias is significantly greater than the x-ray emissions measurement resulting from scanning via 309, via 309 is characterized as having a void. It should be noted that the control measurement can be determined at any time. For example via 309 may be scanned well before a control measurement can be determined, since adjacent vias have not yet been scanned. All the vias may be scanned in raster mode and the resulting x-ray emission measurements can stored in the database. After the scan is completed, defect determinations can be made based on the x-ray emission measurements of a particular via and the control measurements determined from x-ray emission levels of adjacent vias. According to other embodiments, after via 309 scanned, the adjacent vias are immediately scanned to determine whether via 309 contains a void.

Voids can be characterized further by varying electron beam intensities and varying the scan target. After a void is detected, an electron beam can be focused on nearby areas immediately neighboring the detected void. The electron beam can be focused on proximate areas by varying the beam potential for void depth characterization or moving the stage or column for length and width characterization. Beam potential can be varied to affect depth measurement. Higher beam potentials allow for greater penetration of the substrate, thereby enabling a deeper probing of the material. Variations in beam potential can provide information for characterizing the location and dimensions of the void.

Figure 4:
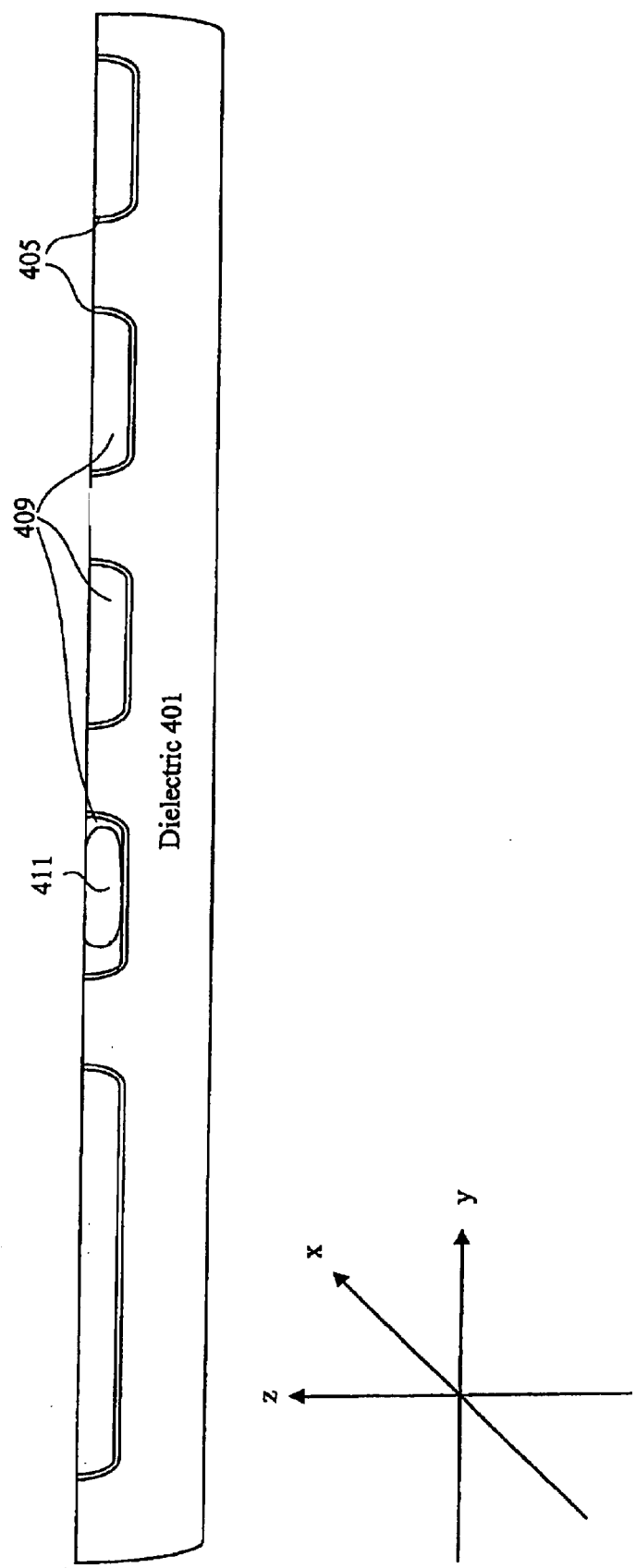
FIG. 4 is a cross-sectional representation of a plurality of vias.

FIG. 4 is a diagrammatic representation of a cross-section of a test sample. The metallization or thin film layer 409 is deposited on top of a barrier layer 405. According to various embodiments, the thin film layer 409 comprises a material such as copper (Cu) or aluminum (Al) and the barrier layer comprises a material such as tantalum (T) or tantalum nitride (TaN). Typically, the metallization or thin film layer 409 is much thicker than the barrier layer 405. A tantalum barrier layer 405 is typically used to prevent the copper from seeping into the dielectric 401. In one embodiment, the thin film layer is 1000 nm while the barrier layer is 15 nm. However, the techniques of the present invention can be used for detecting voids 411 associated with metallization layers 409 and barrier layers 405 of varying thickness.

According to various embodiments, voids are detected and characterized after a metallization layer 409 is deposited onto a barrier layer 405. The energy of the scan by an x-ray emission inducer such as an electron beam is varied based on the nominal thickness of the thin film layer. The electron beam energy is varied to generate the maximum x-ray emission intensity from the first surface of the sample. If the electron beam energy is insufficient, few electrons will penetrate the surface of the sample and interact with the conductive material, such as copper, to emit x-rays with energy levels characteristic of copper. As will be appreciated by one of skill in the art, electrons interacting with a conductive material such as copper emit K-line x-rays. Characteristic x-rays will be described further below.

If the electron beam energy is too high, many electrons will penetrate the conductive material completely and interact with an underlying barrier or dielectric material. X-rays may still be emitted due to interaction with a barrier or material such as tantalum, however the energy levels of the emitted x-rays will be characteristic of tantalum and not of copper.

Figure 5:
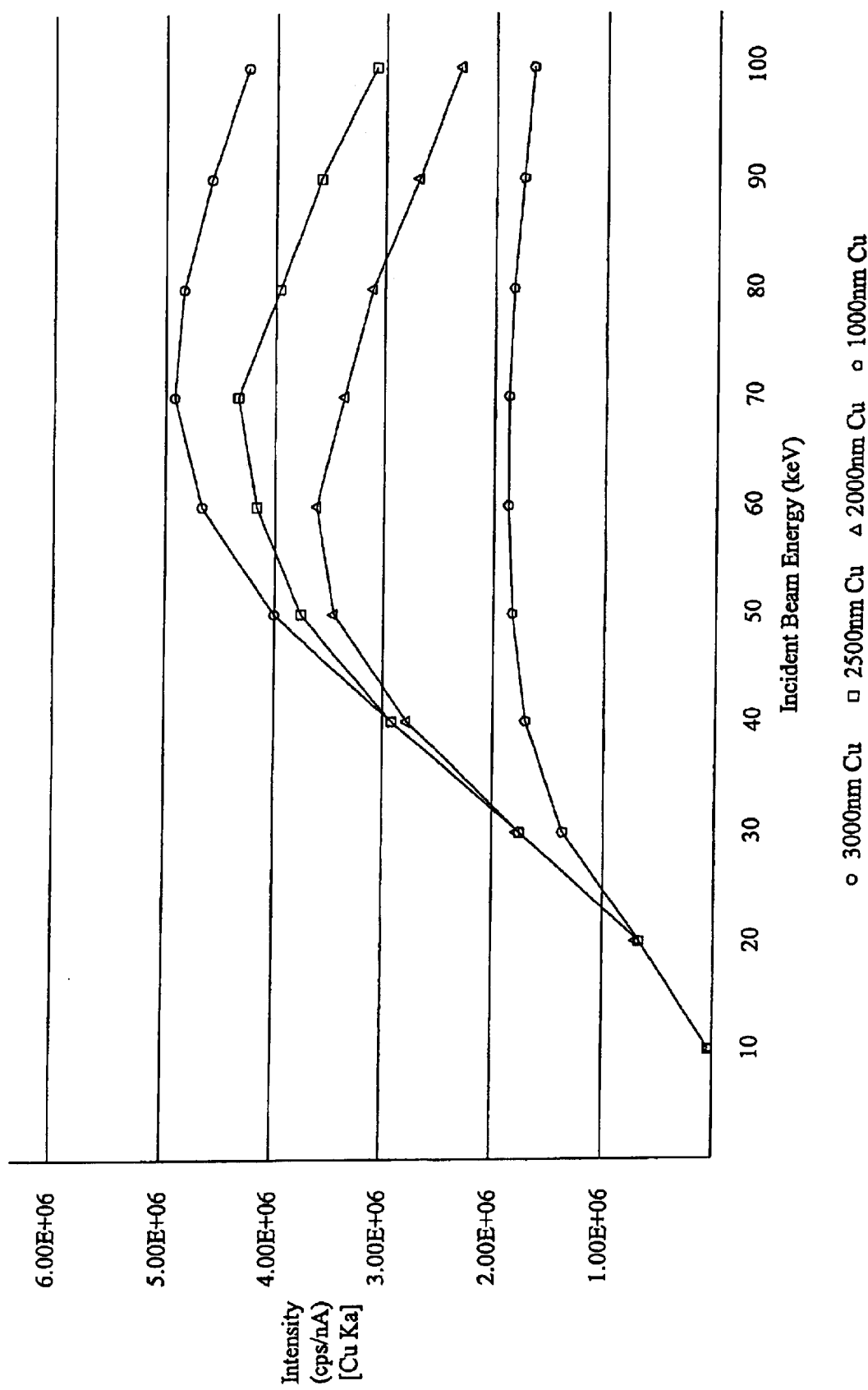
FIG. 5 is a graphical representation of incident beam energies and x-ray emission intensities.

FIG. 5 is a graphical representation showing specific electron beam energies for copper layers of varying thickness. For 1000 nm copper, the x-ray emission intensity is 2.00e+06 cps/nA when the incident beam energy is approximately 40 keV. For 2000 nm copper, the x-ray emission intensity is 3.50e+06 cps/nA when the incident beam energy is approximately 60 keV. It should be noted, that higher incident beam energies are typically used for thicker copper layers. It should also be noted that higher beam energies eventually lead to a decrease in x-ray emission intensity as shown in portion 503.

As noted above, if the incident beam energy is too high, many electrons penetrate the metallization layer completely and interact with the underlying barrier or dielectric layers. Consequently, more x-ray emissions have energy levels corresponding to the underlying barrier materials. In one example, many electrons penetrate the copper layer and interact with the underlying tantalum barrier layer. The x-ray emission energies, consequently, correspond with x-ray emission energies characteristic of tantalum.

A similar effect would occur if there was a void in the copper layer. If there was a void in the copper layer, many electrons would penetrate through the copper layer entirely and interact with the underlying layers. More x-ray emissions characteristic of tantalum would be detected. This provides a convenient technique for confirming the existence of a void. A scan target without a void would produce many x-ray emissions characteristic of copper and fewer x-ray emissions characteristic of tantalum. However, a scan target with a void would produce fewer x-ray emissions characteristic of copper and more x-ray emissions characteristic of tantalum, because the electrons would penetrate the copper layer entirely and interact with the underlying tantalum layer.

To detect x-ray emissions from different materials a single detector or multiple detectors can be used as the x-ray detection system. X-ray detection systems are described in more detail below.

Another technique for detecting, characterizing, or confirming the existence of a void is to measure the amount of electrons that penetrate the test sample completely. Electrons penetrating the test sample completely can generate a current that can be detected by an electrically isolated stage. Techniques for detecting and characterizing voids by measuring the intensity of electrons completely penetrating the sample are described in concurrently filed U.S. patent application Ser. No. 09/990,170 by Mehran Nasser-Ghodsi and Jeffrey Reichert, and titled Methods and Apparatus for Void and Erosion Localization, the entirety of which is incorporated herein by reference for all purposes.

Figure 6:
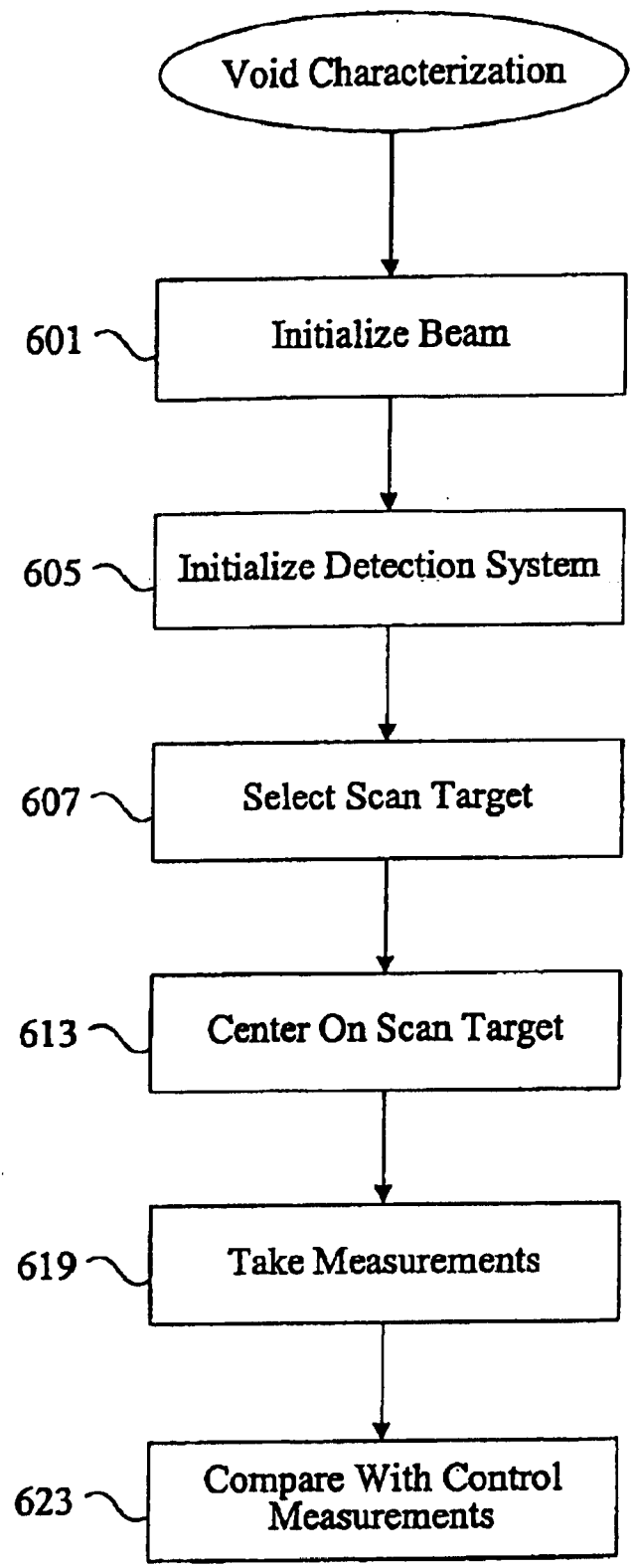
FIG. 6 is a process flow diagram showing the scanning of a sample.

FIG. 6 is a process flow diagram showing the detection and characterization of a void according to specific embodiments. At 601, an x-ray emission inducer is initialized. Initializing the x-ray emission inducer may involve setting the electron beam energy based on the thickness of a thin film layer under test. The beam energy can be set as noted above with reference to FIG. 5.

The x-ray emission detectors can be initialized at 605. Initializing the detectors can include setting the detectors to measure characteristic x-ray emissions from particular materials such as copper or tantalum. As will be appreciated by one of skill in the art, the detectors can be spectrometers configured to detect K-line and L-line emissions. A standard sample can be scanned using the x-ray emission inducer as part of the initialization process at 605. In one embodiment, a layer of copper having a predetermined thickness is scanned so that characteristic x-ray emissions are measured by the detectors at 605. The standard measurement can be used to tune the x-ray detectors to set detector sensitivity. A variety of calibration and initialization techniques can be used. According to various embodiments, initialization of the inducer at 601 and the detectors at 605 is performed before each wafer is tested. According to other embodiments, initialization occurs again after a number of wafers are scanned.

At 607, the x-ray emission inducer is directed at the scan target. The scan target may be an area of interest as determined by the voltage contrast technique. The scan target may also be any area that may contain a void. The inducer can be directed at the scan target by moving the stage or by moving the inducer. At 613, a suspect via is centered in the frame of view of the x-ray emission inducer. Centering the via may include orienting the long axis of the via with the x-axis of the stage. Centering the via may also include rotating the stage.

The via is scanned by an x-ray emission inducer, such as electron beam, and the x-ray emission intensity is measured at 619. According to various embodiments, the x-ray emission detector system is located alongside the x-ray emission inducer on the top side of the sample.

The x-ray emission counts are compared with a control measurement in order to determine whether a void is present in the via. According to one embodiment, if the x-ray emission intensity is 25% less than the control measurement, a void is determined to be present. In one example, if the x-ray emission intensity is 2.00E+06 cps/nA while the control measurement is 3.00E+06 cps/nA, a void is determined to be present. The control measurement can be determined in a number of different ways. According to one embodiment, after the x-ray intensity is measured, the neighboring vias are scanned and the x-ray emission counts corresponding to the neighboring vias are determined. For example, after the first via is scanned and the x-ray emission counts determined, the neighboring +x, −x, +y, and −y vias are scanned and the corresponding x-ray emission counts measured. Subsequently, the neighboring +2x, −2x, +2y, −2y vias are scanned as well. As noted above, the x-ray emission counts corresponding to the neighboring vias can be used to determine a control measurement. Alternatively the control measurement may be a value stored in the database determined from another process or from scans of certain neighboring vias such as +x, +y, −x, −y, etc. In one embodiment, the x-ray emissions from a via and the x-ray emissions from adjacent vias can be compared graphically.

Figure 7A:
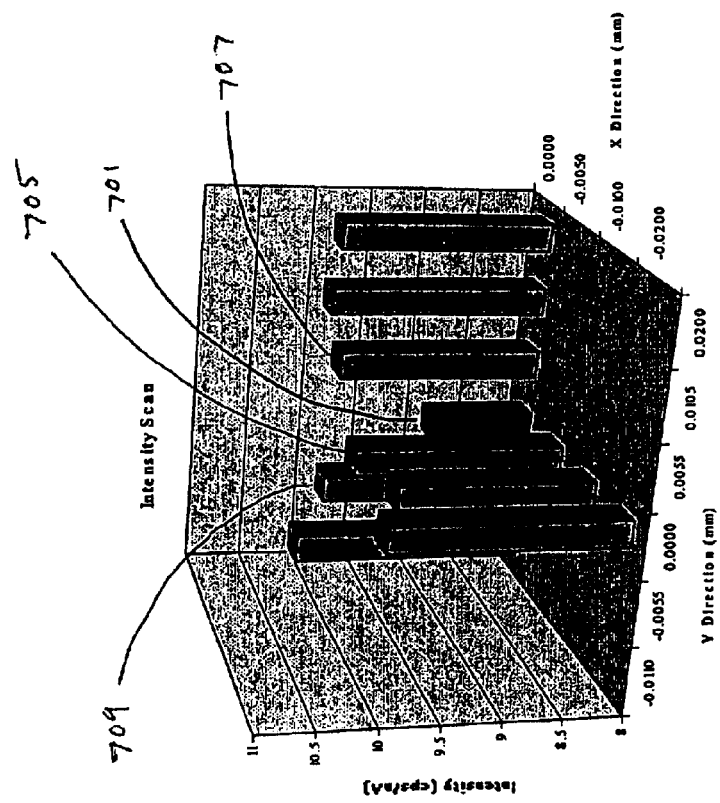
FIGS. 7A and 7B are graphical representations of x-ray emissions from a scan target and adjacent scan targets.
Figure 7B:
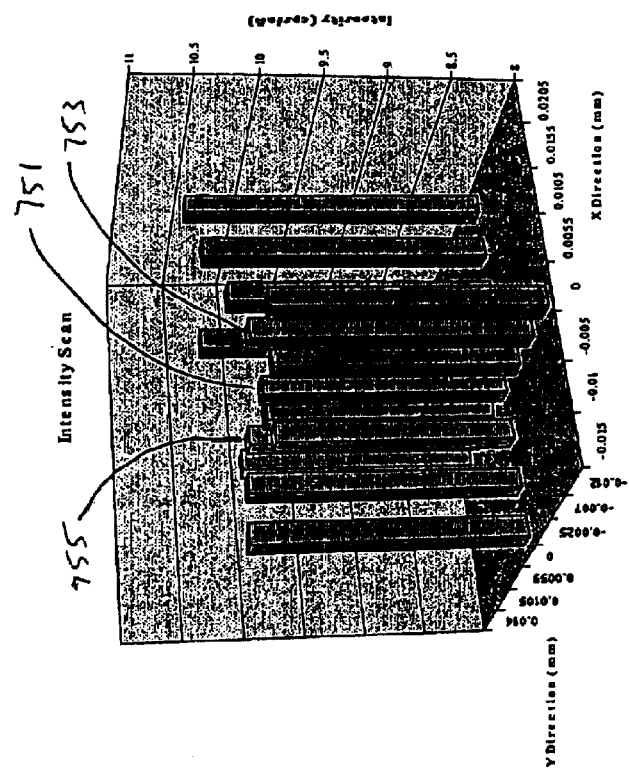

FIGS. 7A and 7B are graphical representations of the electron emissions resulting from scans of a via and the adjacent vias. FIG. 7A is a graphical representation of an x-ray emission intensity scanned for a via having a void. A scan of a via result in x-ray emission intensity 701. The x-ray emission intensity 701 is significantly less than the x-ray emission intensities 707, 705, and 709, corresponding to +y, −x, and −y. By contrast, FIG. 7B is a graphical representation of a via without a void. It should be noted that the x-ray emission intensity 751 is similar to the x-ray emission intensity measurements 753 and 755 of neighboring vias.

Figure 8:
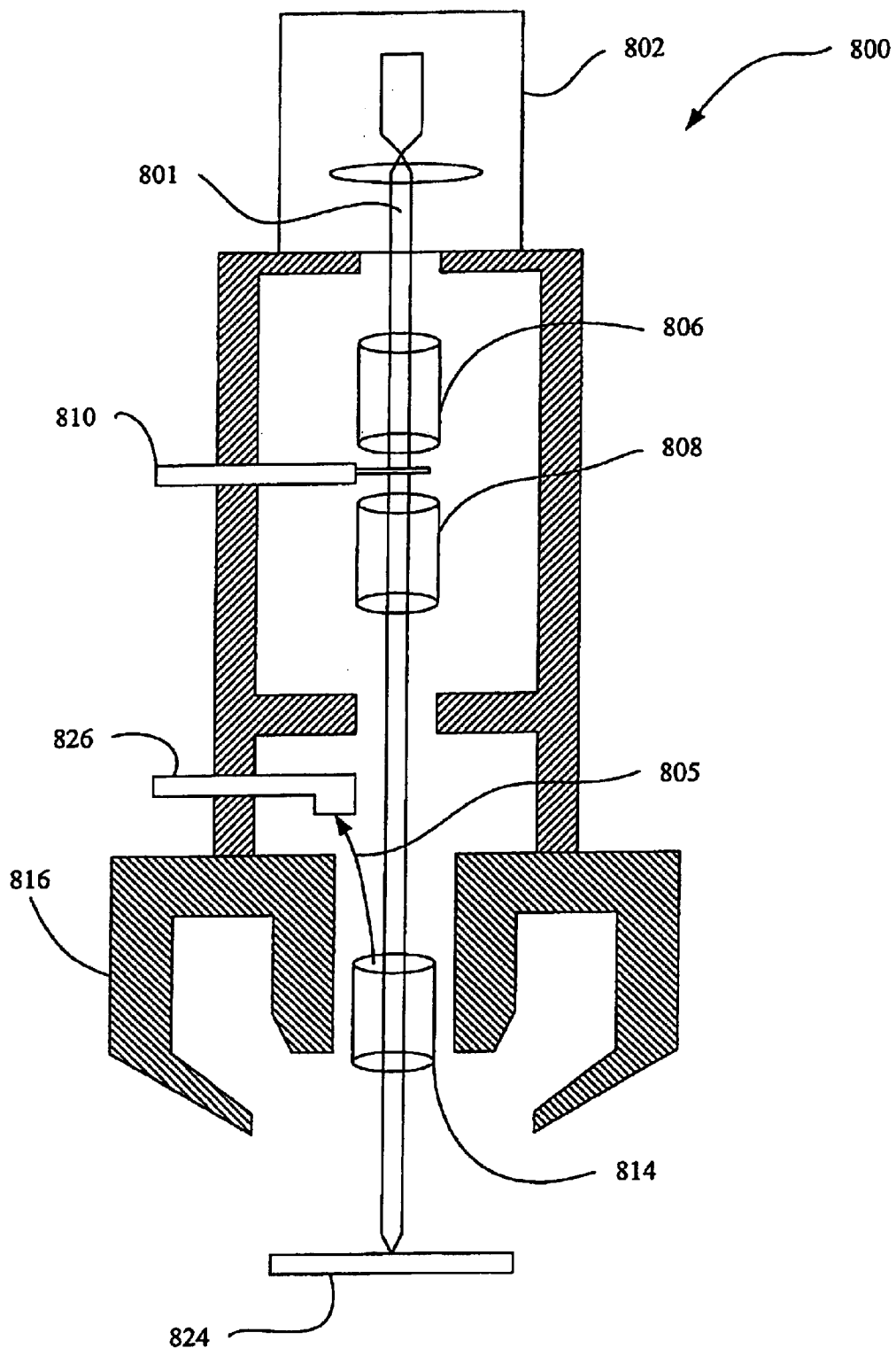
FIG. 8 is a diagrammatic representation of an electron beam that can be used to implement scanning of a sample.

An x-ray emission inducer may be anything that causes X-rays to emanate from the sample under test. In one embodiment, the x-ray emission inducer can be a scanning electron microscope (SEM). FIG. 8 is a diagrammatic representation of a scanning electron microscope (SEM) 800. As shown, the SEM system 800 includes an electron beam generator (802 through 816) that generates and directs an electron beam 801 substantially toward an area of interest on a specimen 824.

In one embodiment, the electron beam generator can include an electron source unit 802, an alignment octupole 806, an electrostatic predeflector 808, a variable aperture 810, a wien filter 814, and a magnetic objective lens 816. The source unit 802 may be implemented in any suitable form for generating and emitting electrons. For example, the source unit 802 may be in the form of a filament that is heated such that electrons within the filament are excited and emitted from the filament. The octupole 806 is configured to align the beam after a particular gun lens voltage is selected. In other words, the beam may have to be moved such that it is realigned with respect to the aperture 810.

The aperture 810 forms a hole through which the beam is directed. The lower quadrupole 808 may be included to compensate for mechanical alignment discrepancies. That is, the lower quadrupole 808 is used to adjust the alignment of the beam with respect to any misaligned through-holes of the SEM through which the beam must travel. The magnetic objective lens 816 provides a mechanism for accelerating the beam towards the sample.

Figure 9:
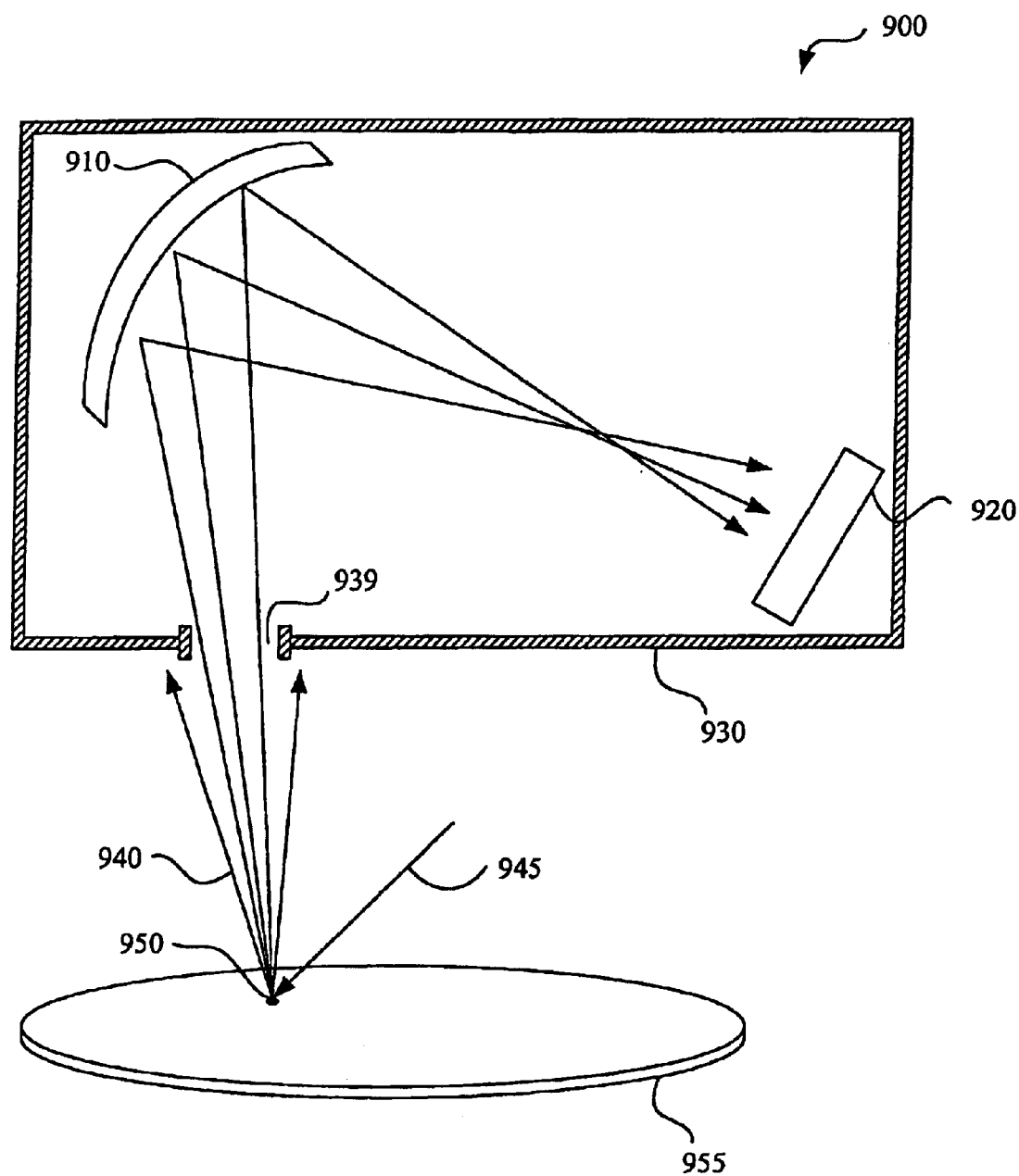
FIG. 9 is a diagrammatic representation of a detector that can be used to measure x-ray emissions.

Any suitable detector for measuring x-rays may be used to detect x-rays emitted from the sample. FIG. 9 is a cross-sectional representation of a wavelength dispersive system (WDS) x-ray detector in accordance with one embodiment of the present invention. Each x-ray detector 900 includes a housing 930 having an aperture 939. The housing and aperture are optional for practicing the techniques of the present invention. An electron beam 945 is directed to a focus point 950 on a thin film device 955 (i.e., a semiconductor wafer). The electron beam 945 causes photons 940 to emanate from the focus point 950. The aperture 939 permits a limited amount of photons 940 to enter each detector 900. Upon entering the detector 900, each photon travels along a path to a concave reflective surface 910. The reflective surface 910 directs a portion of photons to a sensor 920. The reflective surface 910 is designed and positioned so that only photons with a specific energy level are directed to the sensor 920. The reflective surface 910 may be positioned to direct only photons with an energy level characteristic of a certain material to facilitate a film characterization process. By detecting photons of only a specific energy level, detector 900 is capable of obtaining high signal to noise ratios. It should be noted that the reflective surface may be a Bragg reflector or a crystal capable of directing photons towards the sensor.

Figure 10:
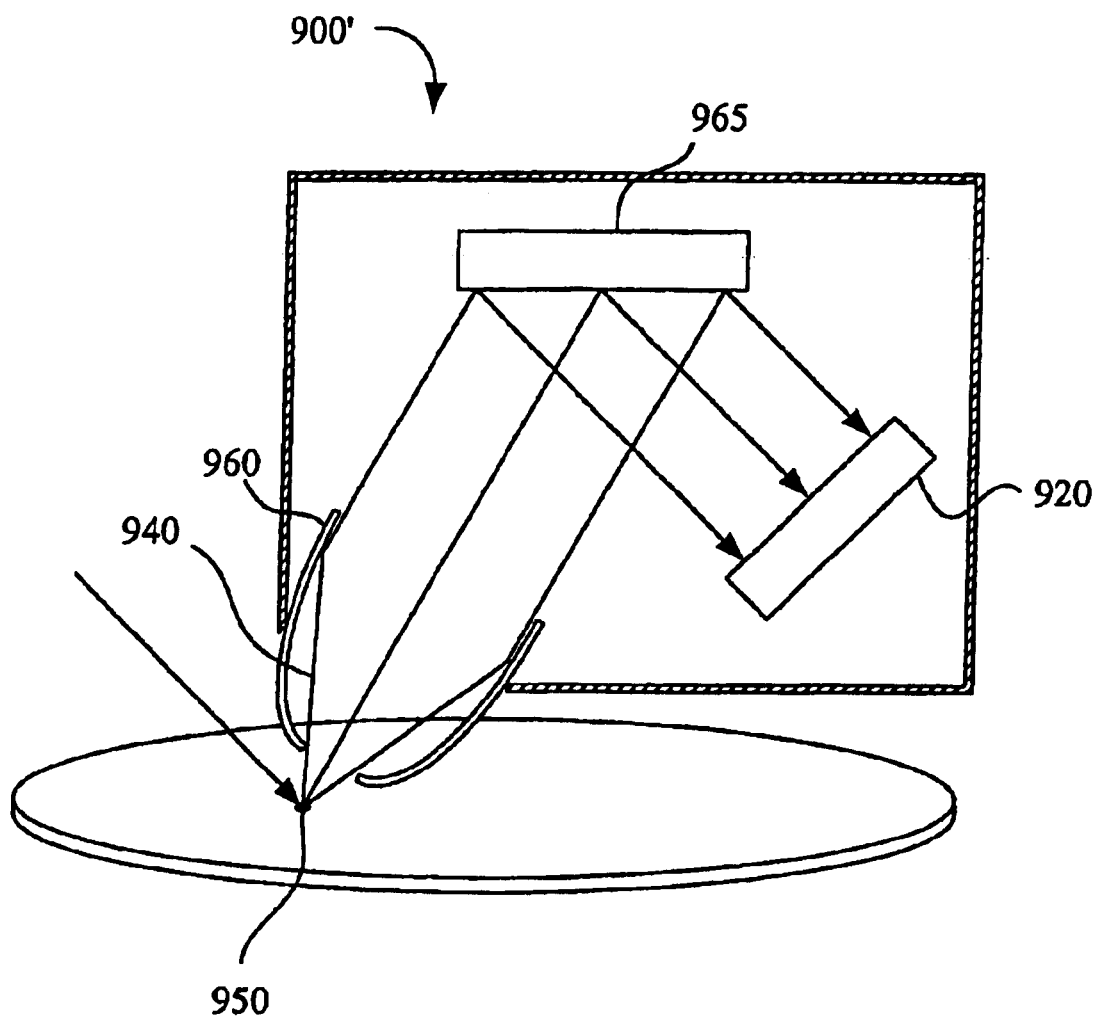
FIG. 10 is a cross-sectional view of a detector that can be used.

A cross-sectional view of an alternative embodiment of a WDS X-ray detector 900' is illustrated in FIG. 10. Detector 900' has a collimator 960 that captures the photons 940 emanating from the focus point 950, and then through its reflective surfaces causes the photons 940 to travel in substantially parallel paths. The collimator 960 is generally made from metal foil material. The photons then reflect off of a substantially flat reflective surface 965 such that the photons 940 continue in parallel paths towards the sensor 920. Similarly with detector 900, the reflective surface 965 in detector 900' may also be Bragg reflector or a crystal.

A common device which contains the general elements of the detector 900 and 900' is a Wavelength Dispersive System (WDS). By utilizing multiple WDS detectors, one or more photon peaks may be detected for each type of material that is expected to be present within the measured film stack of the specimen. That is, characteristic emission levels for one or more types of material in the film stack may be measured. One or more individual detectors may also be dedicated to detect the various characteristic emission levels for each type of material. For example, two WDS detectors may be dedicated for detecting two peaks associated with a copper material. As described earlier each material has emission levels characteristic of photons released due to an electron falling from each of the K, L, or M shells. By using multiple WDS detectors, the test system is able to obtain information for each of a multiple number of film layers.

Another type of detector, an Energy Dispersive System (EDS), collects photons in a wide spectrum of energies. EDS are capable of collecting a greater range of signals. As a result however, EDS detectors also collect photons having energies surrounding the characteristic photon energies. This causes EDS detectors to have lower signal to noise ratios.

The test system of the illustrated embodiment is capable of obtaining measurements having precision within 0.5% accuracy. Thus, the test system allows for both accurate characterization and a high throughput rate.

Although the foregoing invention has been described in some detail for purposes of clarity of understanding, it will be apparent that certain changes and modifications may be practiced within the scope of the appended claims. The techniques of the present invention can be applied to void characterization, but can also be used for thin-film measurement as described in U.S. patent application Ser. No. 09/695,726 by Shing Lee, and titled Film Thickness Measurement Using E-Beam Induced X-Ray Microanalysis as of filing on Oct. 23, 2000, the entirety of which is incorporated herein by reference for all purposes.

It should be noted that there are many alternative ways of implementing the techniques of the present invention. For example, prior to performing comparisons between x-ray emission measurements and control measurements, an entire wafer may be scanned and the corresponding emission measurements stored. The comparisons can then be performed after the entire wafer is scanned and the control measurement can be determined using emission measurements from the entire wafer. Accordingly, the present embodiments are to be considered as illustrative and not restrictive, and the invention is not to be limited to the details given herein, but may be modified within the scope and equivalents of the appended claims.

What is claimed is:

1. An apparatus for characterizing a void in a first scan target associated with a sample, the sample having a first surface and a second surface, the apparatus comprising:
    an x-ray emission inducer configured to scan a first scan target, the x-ray emission inducer causing the first scan target to emit x-rays from the first surface;
    a current detection system configured to measure generated current caused by the x-ray emission inducer on an electrically isolated stage to obtain generated current information;
    an x-ray emission detection system configured to obtain a measurement of the x-rays emitted from the first surface of the sample, wherein the x-ray is compared to a control measurement to obtain comparison information used with generated current information to characterize a void in the first scan target.

2. The apparatus of claim 1, further comprising a stage configured to secure the sample, wherein the stage is configured to position the sample relative to the x-ray emission inducer.

3. The apparatus of claim 2, wherein positioning the sample comprises rotating the sample.

4. The apparatus of claim 2, wherein the first scan target comprises a via.

5. The apparatus of claim 4, wherein the sample is a wafer comprising a plurality of integrated circuits.

6. The apparatus of claim 1, wherein the x-ray emission detection system is configured to detect x-rays with a first emission energy corresponding to the first material.

7. The apparatus of claim 6, wherein the first material comprises Cu.

8. The apparatus of claim 7, wherein the x-ray emission detection system is further configured to detect x-rays with a second emission energy corresponding to the second material.

9. The apparatus of claim 8, wherein the second material comprises Ta.

10. The apparatus of claim 9, wherein the control measurement is obtained by scanning an adjacent scan target.

11. A system for characterizing voids associated with a sample, the sample having a first surface and a second surface, the system comprising:
    memory;
    a processor coupled with memory, the processor configured to measure generated current caused by an x-ray emission inducer on an electricaly isolated stage to obtain generated current information identify a first measurement of induced x-ray emissions characteristic of a first material at a first scan target, identify a control measurement, and provide the first measurement and the control for comparison to thereby obtain comparison information used with generated current information for characterizing a void associated with the first scan target in the sample.

12. The system of claim 11, wherein the first material has low resistivity.

13. The system of claim 12, wherein the first material is copper.

14. The system of claim 11, wherein the sample is a wafer comprising a plurality of integrated circuits.

15. The system of claim 11, further comprising identifying a second measurement of x-ray emissions characteristic of a second material.

16. The system of claim 11, wherein the second material is a barrier material.

17. The system of claim 16, wherein the second material is Ta.

18. The system of claim 11, wherein characterizing voids associated with the sample comprises determining the size and location of a void.

19. The system of claim 11, wherein the control measurement is obtained by scanning an adjacent scan target.

20. The system of claim 19, wherein the scan target is a via.

21. The system of claim 20, wherein the adjacent scan target is an adjacent via.

22. The system of claim 21, wherein the control measurement is obtained by scanning adjacent vias in the +x, −x, +y, and −y positions.

23. The system of claim 22, wherein the control measurement is obtained by scanning adjacent vias in the +2x, −2x, +2y, and −2y positions.

24. A method for characterizing a void in a sample, the method comprising:
    measuring generated current on an electrically isolated stage to obtain generated current information, the generated current caused by an x-ray emission inducer;
    identifying a first measurement of induced x-ray emissions characteristic of a first material at a first scan target;
    identifying a control measurement;
    providing the first measurement and the control measurement for comparison to thereby obtain comparison information used with generated current information for characterizing a void associated with the first scan target in the sample.

25. The method of claim 24, wherein the first material has low resistivity.

26. The method of claim 25, wherein the first material is copper.

27. The method of claim 24, wherein the sample is a wafer comprising a plurality of integrated circuits.

28. The method of claim 24, further comprising identifying a second measurement of x-ray emissions characteristic of a second material.

29. The method of claim 24, wherein the second material is a barrier material.

30. The method of claim 29, wherein the second material is Ta.

31. The method of claim 24, wherein characterizing voids associated with the sample comprises determining the size and location of a void.

32. The method of claim 24, wherein the control measurement is obtained by scanning an adjacent scan target.

33. The method of claim 32, wherein the scan target is a via.

34. The method of claim 33, wherein the adjacent scan target is an adjacent via.

35. The method of claim 34, wherein the control measurement is obtained by scanning adjacent vias in the +x, −x, +y, and −y positions.

36. The method of claim 35, wherein the control measurement is obtained by scanning adjacent vias in the +2x, −2x, +2y, and −2y positions.

37. An apparatus for characterizing a void in a sample, the apparatus comprising:
    means for measuring generated current on an electrically isolated stage to obtain generated current information, the generated current caused by an x-ray emission inducer;

means for identifying a first measurement of induced x-ray emissions characteristic of a first material at a first scan target;

means for identifying a control measurement;

means for providing the first measurement and the control measurement for comparison to thereby obtain comparison information used with generated current information for characterizing a void associated with the first scan target in the sample.

38. The apparatus of claim 37, wherein the control measurement is obtained by scanning an adjacent scan target.

39. The apparatus of claim 38, wherein the adjacent scan target is an adjacent via.

40. The apparatus of claim 39, wherein the control measurement is obtained by scanning adjacent vias in the +x, −x, +y, and −y positions.

41. The apparatus of claim 40, wherein the control measurement is obtained by scanning adjacent vias in the +2x, −2x, +2y, and −2y positions.

* * * * *

UNITED STATES PATENT AND TRADEMARK OFFICE
CERTIFICATE OF CORRECTION

PATENT NO. : 6,801,596 B2
DATED : October 5, 2004
INVENTOR(S) : Nasser-Ghodsi et al.

It is certified that error appears in the above-identified patent and that said Letters Patent is hereby corrected as shown below:

Column 11,
Line 18, change "x-ray is" to -- x-ray measurement is --.
Line 55, change "control for" to -- control measurement for --.

Signed and Sealed this

First Day of February, 2005

JON W. DUDAS
*Director of the United States Patent and Trademark Office*